(12) United States Patent
Delack

(10) Patent No.: US 7,666,893 B2
(45) Date of Patent: Feb. 23, 2010

(54) METHOD FOR TREATMENT OF NEURODEGENERATIVE DISORDERS

(75) Inventor: Elaine A. Delack, Stanwood, WA (US)

(73) Assignee: MedDEV Inc., Bellingham, WA (US)

( * ) Notice: Subject to any disclaimer, the term of this patent is extended or adjusted under 35 U.S.C. 154(b) by 227 days.

(21) Appl. No.: 11/805,624

(22) Filed: May 23, 2007

(65) Prior Publication Data

US 2007/0276021 A1 Nov. 29, 2007

Related U.S. Application Data

(60) Provisional application No. 60/808,032, filed on May 23, 2006.

(51) Int. Cl.
*A01N 43/50* (2006.01)
*C07D 233/00* (2006.01)
*C07D 233/02* (2006.01)

(52) U.S. Cl. .................. 514/396; 548/300.1; 548/335.1

(58) Field of Classification Search ................. 514/396; 548/300.1, 335.1
See application file for complete search history.

(56) References Cited

U.S. PATENT DOCUMENTS

| | | | |
|---|---|---|---|
| 4,055,573 | A | 10/1977 | Mendelson |
| 6,277,402 | B1 | 8/2001 | DeLack |
| 6,359,145 | B1 | 3/2002 | Terasaka et al. |
| 6,426,360 | B1 * | 7/2002 | Weier et al. ................. 514/396 |
| 6,596,738 | B1 | 7/2003 | Terasaka et al. |
| 6,617,324 | B1 | 9/2003 | Naraian et al. |

OTHER PUBLICATIONS

Alcazar et al. (1998). Induction of apoptosis by cerebrospinal fluid from patients with primary-progressive multiple sclerosis . . . Neuroscience Letters, 255, pp. 25-78.
Aulkemeyer et al. (2000). The small sodium-channel blocking factor in cerebrospinal fluid of multiple sclerosis patients . . . Journal of Neurological Science, 172(1), pp. 49-54.
Baslow, M.H. (1998). Function of the N-acetyl-L-histidine system in the vertebrate eye. Journal of Molecular Neuroscience, 10(3), pp. 193-208.
Behan et al. (2002) The pathogenesis of multiple sclerosis revisited. J R College of Physicians Edinb, 32, pp. 244-265.
Blaustein, M.P. (1975). Effects of potassium, veratridine, and scorpion venom on calcium accumulation and transmitte . . . Journal of Physiology, 247(3), pp. 617-655.
Carvounis, C.P. (1985). Importance of amino acids on vasopressin-stimulated water flow. Journal of Clinical Investigation, 76(2), pp. 779-788.
Chua et al. (2002). MRI findings in osmotic myelinolysis. Clinical Radiology, 57(9), pp. 800-806.
Cid et al. (2002). Neronal apoptosis induced by cerebropional fluid from multiplsclerosis patients . . . Journal of Neurological Science, 193(2), pp. 103-109.

Davies et al. (1998). Hypoosomolarity induces an increase of extracellular N-acetylaspartate concentrationin the rat striatum. Neurochemical Research, 23(3), pp. 1021-1025.
Davis et al. (2002). Glial fibrillary acidic portein in late life major depressive disorder . . . Journal of Neurology Neurosurgery Psychiatry, 73(5), pp. 556,560.
Fields, R.D. (2004). The other half of the brain: Mounting evidence suggests that glilal cells, overlooked for half a century, may . . . Scientific Amercian, pp. 54-61.
Gehl et al. (2004). Biosynthesis of NAAG by an enzyme-mediated process in rat central nervous system neurons and glia. Journal of Neurochemistry, 90(4), pp. 989-997.
Hertz et al. (2004). Astrocytic adrenoceptors: A major drug target in neurological and psychiatric . . . Current Drug Targets CNS Neurological Disorders, 3(3), pp. 239-267.
Huang et al. (2000). Transport of N-acetylasparate by the Na(+)-dependent high-affinity dicarboxylate . . . Journal of Pharmacology Experimental Therapies, 295(1), pp. 392-403.
Kashon et al. (2004). Associations of cortical astrogliosis with cognitive performance and demetia . . . Journal of Alzheimer's Disease, 6(6), pp. 595,604; discussion 673-681.
Kiline et al. (2002). Osmotic myelinolysis in a normonatremic patient. Acta Neurology Belgium, 102(2), pp. 87-89.
Koller et al. (1996). Cerebrospinal fluid from multiple sclerosis patients inactivates neuronal Na+ current. Brain, 119(Pt 2), pp. 457-463.
Mews et al. (1998). Oligodendrocyte and axon pathology in clinical silent multipel sclerosis lesions. Multiple Sclerosis Journal, 4(2), pp. 55-62.
Oliveira et al. (2004). Alterations in the central vasopressin and oxytocin axis after lesion of a brina osmotic sensory region. Brain Research Bulletin, 63(6), pp. 515,520.
Perea et al. (2005). Synaptic regulation of the astrocyte calcium signal. Journal of Neurl Transmission, 112(1), pp. 127-135.

(Continued)

*Primary Examiner*—Sreeni Padmanabhan
*Assistant Examiner*—Sarah Pihonak
(74) *Attorney, Agent, or Firm*—Todd N. Hathaway

(57) ABSTRACT

A method for treatment of multiple sclerosis and other neurodegenerative diseases, disorders or conditions. An alkyl ester of imidazole carboxylic acid, preferably methyl 4-imidazolecarboxylate, is administered in a therapeutic amount. It is hypothesized that the alkyl ester of imidazole carboxylic acid serves to restore and/or maintain the intracellular/extracellular osmolyte gradient in the central nervous system (CNS). The methyl 4-imidazolecarboxylate may be administered transdermally, using PLO gel or other suitable transdermal carrier. The compound may also be administered orally, inhaler or by injection. The treatment is advantageously performed on a three day cycle, with a period of two days intervening between each day on which the compound is administered. Dosage ranges may be from about 0.01 mcg to about 3.0 mcg, with dosages in the range from about 0.1 mcg to about 0.2 mcg in generally preferred when using transdermal administration.

8 Claims, No Drawings

OTHER PUBLICATIONS

Ramsey et al. (1984). The defence of plasma osmolaity. Journal of Physiology (Paris), 79(6), pp. 416-420.

Sager et al. (1999). Astroglia contain a specific transport mechanism for N-acetyl-L-aspartate. Journal of Neurochemistyr, 73(2), pp. 807-811.

Schiepers et al. (1997). Positron emission tomography, magnetic resonance imaging and proton NMR . . . Multiple Sclerosis Journal, 3(1), pp. 8-17.

Sharma et al. (1992). Histamine modulates heat stress-induced changes in blood-brain barrier permeability, cerebral blood flow . . . Neurosceince, 50(2), pp. 445, 454.

Simard et al. (2004). The nerobiology of glia in the context of waer and ion homeostatis. Neuroscience, 129(4), pp. 877-896.

Tateishi et al. (2006). S100B: astrocyte specific protein. Nihon Schinkei Seishin Yakurigaku Zassi, 26(1), pp. 6-11.

Vivekanandhan et al. (2005). Adenosine deaminase and 5'nuclotidiase activities in peripheral blood T cells . . . Neurochemistry Research, 30(4), pp. 453-456.

Williamson et al. (1988). Calcium-dependent release of N-acetylaspartylglutamate from retinal nerons upon depolarization. Brain Research, 475(1), pp. 151-155.

* cited by examiner

METHOD FOR TREATMENT OF NEURODEGENERATIVE DISORDERS

RELATED APPLICATIONS

This application claims the benefit of U.S. Provisional Patent Application No. 60/808,032 filed on May 23, 2006.

BACKGROUND OF THE INVENTION a. Field of the Invention

The present invention relates generally to methods for the treatment of multiple sclerosis and other neurodegenerative diseases, disorders and conditions, and more particularly to treatment of such multiple neurodegenerative diseases, disorders and conditions by administration of an alkyl ester of imidazole carboxylic acid in order to maintain the intracellular/extracellular osmolyte gradient in the central nervous system (CNS).

b. Background

Multiple sclerosis (MS) is a neurodegenerative disease of the central nervous system resulting in sensory and motor dysfunction, visual disturbances, cognitive and memory impairment, and bowel and bladder dysfunction. Multiple sclerosis is the most common neurological disorder of young adults with the onset of symptoms generally occurring between the ages of 20 and 50. According to the National Multiple Sclerosis Society, the disease currently affects more than 400,000 individuals in the United States with 200 new cases diagnosed every week and more than 2.5 million people worldwide. Data from the recent Zogby International poll suggests that these numbers are underestimated and that multiple sclerosis affects 2.87 million individuals in the United States and more than 6.25 million worldwide. Over 70% of all multiple sclerosis patients are too disabled to remain in the workforce due to symptoms of fatigue and cognitive dysfunction. A recent study by Duke University estimates annual direct and indirect costs of MS in the United States to be $9 billion; this makes it second only to Alzheimer's disease in economic impact.

The cause of multiple sclerosis still eludes science, but it has been postulated that it is an autoimmune disease in which the immune system attacks and destroys the myelin in the central nervous system. Thus, the FDA approved medications for multiple sclerosis are all aimed at suppressing the immune system, but unfortunately these treatments have failed to have any beneficial effect on the debilitating symptoms associated with multiple sclerosis. Recent research published in 2002 by Dr. Behan, Professor Emeritus of Clinical Neurology, and colleagues, shows that multiple sclerosis is not an autoimmune disease in which the immune system is attacking the myelin. Behan et al, proved via MR Spectroscopy that the oligodendrocytes (the myelin producing cells in the central nervous system) underwent degeneration up to three weeks before any immune cells were present at the site of degeneration.

In addition to MS, there are many other neurological diseases and disorders that may stem from possibly similar degenerative mechanisms. Examples include, but are not limited to, fibromyalgia, memory impairment, and certain forms of depression and erectile dysfunction.

Accordingly, there exists a need for a method for treating neurodegenerative diseases, disorders and conditions, such as multiple sclerosis, that yields beneficial results, and that is not founded on the previous autoimmune hypothesis. Furthermore, there exists a need for such a method that yields rapid, substantial and sustained benefits to patients. Still further, there is this need for such a method in which the treatment can be applied to patients on an economical basis and without undue difficulty.

SUMMARY OF INVENTION

The present invention has solved the problems cited above, and is a method for treating neurodegenerative diseases by addressing the intracellular/extracellular osmolyte gradient in the central nervous system. Examples of neurodegenerative diseases, disorders and conditions that can be treated by the method of the present invention include, but are not limited to, multiple sclerosis, fibromyalgia, memory impairment, erectile dysfunction and depression.

Broadly, the method comprises the step administering to a patient suffering from a neurodegenerative disease, disorder or condition, an effective amount of at least one alkyl ester of imidazole carboxylic acid. Preferably, the at least one alkyl ester of imidazole carboxylic acid is administered in an amount sufficient to maintain the intracellular/extracellular osmolyte gradient in the CNS within a substantially normal range.

The at least one alkyl ester of imidazole carboxylic acid may be methyl 4-imidazolecarboxylate. The methyl 4-imidazolecarboxylate may be administered orally, by inhaler, by injection, or by transdermal application, or combinations thereof. When administered by transdermal application, the dosage range of the methyl 4-imidazolecarboxylate may be from about 0.01 mcg to about 3.0 mcg per day, with a preferred dosage range being from about 0.1 mcg to about 0.2 mcg per day.

These and other features and advantages of the invention will be more fully appreciated from reading of the following detailed description.

DETAILED DESCRIPTION

The present invention provides a method for treatment of multiple sclerosis and other neurodegenerative diseases, disorders and conditions by one or more the administration of alkyl esters of imidazole carboxylic acid, preferably methyl 4-imidazolecarboxylate, in amounts sufficient to maintain the intracellular/extracellular osmolyte gradient in the CNS.

Much of the following description discusses the invention in the context of multiple sclerosis, which is one of the most widespread and serious diseases to which the treatment is directed, and for which significant amounts of research data is available. However, it will be understood that the present invention is not limited to the treatment of MS, and that the invention includes the treatment of other neurodegenerative diseases, disorders and conditions, including, without limitation, fibromyalgia, erectile dysfunction, memory impairment and depression.

a. HYPOTHESIS AND MECHANISM

As noted above, the previous belief that multiple sclerosis (and related conditions) is an autoimmune disease, has not been born out by clinical results and recent research. Rather, as part of the present invention, it is hypothesized that the oligodendrocyte destruction is not caused by an autoimmune condition, but is instead due to the efflux of potassium ions (K+) out of the cells as a result of deficient maintenance of the intracellular/extracellular osmolyte gradient. The inventor herein hypothesizes that the dysfunction of the intracellular/extracellular osmolyte gradient is due to inadequate synthesis of imidazole ring derivatives. The present invention teaches the administration of a methyl ester of imidazole carboxylic acid, specifically methyl 4-imidazolecarboxylate, in an amount sufficient to maintain the intracellular/extracellular osmolyte gradient and prevent the self-degeneration of the oligodendroctyes and/or neurons and/or neuronal cells in the central nervous system in multiple sclerosis patients.

Research has proven that communication between cells is carried not only by the neurons and the astrocytes, but also via calcium and sodium ions in the extracellular medium [Fields, R. D. April 2004]. The extracellular fluid provides a bi-directional communication between the astrocytes and the neurons. The information highway between the pre and post synaptic neurons and the surrounding astrocytes is called the tripartite synapse and the information is carried by calcium and sodium ion transporters in the extracellular fluid [Fields, R. D. April 2004; Perea & Araque, 2005]. The movement of the ions in the extracellular fluid is dependent on entropy. Entropy is the movement of all spontaneous reactions toward a condition of greater randomness or greater disorder. Entropy involves the formation of a kosmotropic (highly structured environment) that dissociates to a chaotropic (disorderly environment) [Szent-Gyorgy, March 2005].

The side-chain carboxylate in proteins plays an integral part in forming and maintaining the extracellular medium in the tripartite synapse and the transmission of information via entropy. The side-chain carboxylate groups (i.e. aspartic and glutamic acids) in proteins contain two oxygen atoms that are nearer than occurs between water molecules in bulk liquid water (~2.82 Å). This normally causes a high density water clustering around these groups due to the closeness of the water molecules as they hydrogen bond to these carboxylate oxygen atoms. Such hydrogen bonding induces a more negative charge on the carboxyl oxygen atoms leading to an increase in the carboxylate $pK_a$. It is found that $Na^+$ ions prefer binding to the weaker carboxylate groups ($pK_a>4.5$) whereas $K^+$ ions prefer the stronger acids ($pK_a<3.5$) [G. N. Ling, *Life at the cell and below-cell level. The hidden history of a functional revolution in Biology*, (Pacific Press, New York, 2001).].

The carboxylates form a higher density water network resulting in the sodium ions accumulating in the extracellular medium, whereas the potassium ions prefer a lower density water network and thus accumulate in the intracellular medium. This results in the concentration gradients of sodium and potassium in the extracellular and intracellular mediums respectively. The formation of the higher density water networking by the carboxylates creates a temporary kosmotropic environment, but then as the sodium ions are attracted to the carboxylate synthesized by the neuron and oligodendrocyte, the sodium destroys the hydrogen bonds of the high density water network resulting in entropy. This randomization continues outward from the synapse through the extracellular fluid creating current that flows to the astrocytes. The entropy current moves in the direction of the astroctyes because the carboxylates synthesized by the astrocytes have a high affinity for calcium ions and calcium is even more destructive to the hydrogen bonds formed between the carboxylates and water molecules. This results in even greater entropy around the astrocytes than around the neurons and oligodendroctyes [G. N. Ling, *Life at the cell and below-cell level. The hidden history of a functional revolution in Biology*, (Pacific Press, New York, 2001).

N-acetyl-L-aspartate (NAA) and N-acetyl-L-aspartylglutamate (NAAG) act as cellular water pumps that help to maintain the intracellular/extracellular osmolyte gradient independent of the extracellular solute composition or osmolarity. [Baslow, 1998].

N-acetylaspartate (NAA) is one of the most abundant amino acids in the human brain. It is located in and synthesized by neurons. The extracellular levels of NAA are increased in the presence of hypoosmolarity of the brain [Davies et al, 1998]. NAA levels have been shown to be decreased in MS patients and research has shown a significant correlation between decreased NAA levels and increased expanded disability scores. H2 receptor stimulation, which has been postulated by this inventor to be deficient in MS, is necessary to maintain the proper water content in the brain. Impaired H2 receptor stimulation results in dehydration of the brain, creating a hyperosmolarity of the brain [Sharma et al, 1992]. This may account for the low levels of NAA in the brains of MS patients.

Sodium ions are needed to transport NAA through the extracellular medium via the sodium dependent NaDC3 transporter. The transport of N-acetylaspartate into astrocyte cells is obligatory for its intracellular hydrolysis, a process intimately involved in myelination [Huang et al, 2000]. The neurons synthesize the NAA, which is released into the synapse and then transported in the extracellular fluid via the sodium dependent transporter, NaDC3 to the astrocytes [Sager et al, 1999]. The astrocytes uptake the NAA and utilize it to synthesize N-acetyl-L-aspartylglutamate (NAAG), which is then hydrolyzed to glutamate [Gehl et al, 2004].

Gliosis, an overgrowth of astrocytes in a damaged area of the brain, is common in MS patients and other neurodegenerative diseases such as Alzheimer's, amyotrophic lateral sclerosis, mixed dementia, vascular mediated dementia, depression, cerebral stroke, traumatic brain injury and aging (Kashon et al, 2004; Tateishi et al, 2006). Glial fibrillary acidic protein (GFAP) is a marker for astrogliosis. Cognitive function has been inversely associated with GFAP in the occipital, parietal and temporal lobes. GFAP levels are significantly greater in individuals diagnosed with Alzheimer's disease, mixed dementia, and vascular mediated dementia as compared to non-demented individuals (Kashon et al, 2004). GFAP levels are significantly higher in layer I of the dorsolateral prefrontal cortex in elderly patients with major depressive disorder than in controls (Davis et al, 2002). This increase in astrocytes could result in increased uptake of NAA and increased production of glutamate resulting in the decreased levels of NAA and increased levels of glutamate that are seen in MS patients and other neurodegenerative diseases. Glutamate itself can bind an ammonium ion to form glutamine, a second amino acid. Glutamine can then be recycled to regenerate glutamate. Glycogenolysis and synthesis of glutamate and glutamine from glucose are both metabolic processes restricted to astrocytes [Hertz et al, 2004]. In MS, active lesions and large lesions have increased glucose utilization, increased glutamate concentration and decreased NAA concentration as compared to healthy subjects [Schiepers et al, 1997].

Glutamate is neuroexcitory and elevated levels can be neurotoxic. The release of glutamate by astroctyes is stimulated by extracellular potassium and the release requires the presence of extracellular calcium and the influx (uptake) of the extracellular calcium [Simard & Nedergaard, 2004]. The rate of calcium uptake is increased when the concentration of the potassium is increased [Blaustein, 1975].

Research has shown that MS patients have reduced fast transient sodium currents in the CSF [Aulkemeyer et al, 2000; Koller et al, 1996]. Osmotic myelinolysis is usually associated with hyponatremia [Kiline et al, 2002]. Osmotic myelinolysis is a demyelinating disorder that has similarities to multiple sclerosis, including cerebral white matter and pontine lesions that were hypo and hyper-intense on T1 and T2W sequences respectively [Chua et al, 2002]. The degree of T1 lesion hypointensity on MRI in MS patients in vivo strongly correlated with the neuronal apoptosis induced by cerebrospinal fluid from MS patients on neuron cultures [Cid et al, 2002]. In 1998 Alcazar et al reported scientific findings that the CSF from primary-progressive MS patients induced neuronal damage to healthy normal cortical neurons in culture and that the neuronal cell damage was not due to tumor necrosis factor (TNF-a) molecules transundated from blood or IgG. The present invention hypothesizes that impaired intracellular/extracellular osmolyte gradient of the CSF in an MS patient may be the factor inducing the neuronal damage in vitro and in vivo.

The inventor herein hypothesizes that decreased synthesis of the histidine derivatives, specifically the imidazole ring molecule that is methylated on the side-chain i.e. methyl 4-imidazolecarboxylate, by the neurons and oligodendrocytes results in an impaired intracellular/extracellular osmolyte gradient. Methyl 4-imidazolecarboxylate ($C_5H_6N_2O_2$) has the following molecular structure:

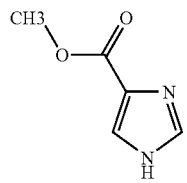

The methyl ester group (—COCH3) is responsible for creating the high-density water networking necessary to maintain the intracellular/extracellular osmolyte gradient.

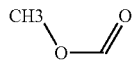

In this functional group, the oxygen atoms are in closer proximity than what normally occurs in bulk water. This creates a higher-density water clustering around these groups. (Water molecules hydrogen-bonded to these oxygens are closer together than they would be in bulk water.)

The inventor herein hypothesizes that the decreased synthesis of the histidine derivatives, specifically decreased synthesis of the methyl ester of imidazole carboxylic acid, i.e. methyl 4-imidazolecarboxylate, by the neurons and oligodendrocytes results in an impaired intracellular/extracellular osmolyte gradient. This in turn results in the failure of the high-density water network forming in the extracellular fluid of the synapse and impedes the accumulation of sodium ions in the extracellular fluid and hinders the initiation of entropy that is necessary for the movement of neurotransmission to the astrocytes. This results in very sluggish to absent neurotransmission via the tripartite synapse system. The deficient formation of the high-density water networking in the extracellular fluid and the deficient concentration of sodium ions in the extracellular fluid results in an efflux of potassium ions into the extracellular fluid which can result in death of the neuronal cell and oligodendroctye. Furthermore, the efflux of potassium ions into the extracellular fluid stimulates the release of glutamate from the astrocytes into the tripartite synapse. Glutamate, a carboxylate synthesized by the astrocytes, creates a high-density water network in the extracellular fluid around the astrocyte and attracts calcium ions to accumulate in the extracellular fluid around the astrocyte. The increased extracellular potassium activates the calcium ion channels in the astroctye membranes resulting in the influx of calcium ions into the astroctye, which results in elevated cytosolic calcium levels in the astroctye. Increased cytosolic calcium stimulates mitosis of astrocytes resulting in gliosis. The increase in the number of astrocytes may result in an increase in the uptake of NAA, resulting in an overall decrease in the NAA levels in the CNS in MS patients.

Consequently, the present invention seeks to maintain the intracellular/extracellular osmolyte gradient in the CSF of patients suffering from MS and other neurodegenerative disorders, by the administration of an alkyl ester of imidazole carboxylic acid methyl 4-imidazolecarboxylate is generally preferred, however, it is anticipated that other alkyl esters of imidazole carboxylic acid may also be suitable and effective. The treatment composition may be administered by any suitable means, such as orally, or by transdermal application, injection or inhaler, to give just a few examples. Administration by transdermal application is preferable in many applicants, in that it provides significant advantages in terms of ease of use, and more consistent dosage levels. Using methyl 4-imidazolecarboxylate, the dosage range is suitably 0.01 mcg to 3.0 mcg per day, with the preferred dosage range being 0.1 mcg to 0.2 mcg per day.

b. FORMULATION

As noted above, transdermal application is generally the preferred mode for administering the methyl 4-imidazolecarboxylate, or other alkyl ester of imidazole carboxylic acid.

Accordingly, material suitable for transdermal application can be prepared using a 1:1000 dilution of methyl 4-imidazolecarboxylate CAS number 17325-26-7, available from Sigma-Aldrich Corporation), combined with a pluronic lecithin organogel transdermal penetration enhancing vehicle, with hydrochloric acid being added to maintain the pH of the solution that or below 3. The resultant mixture may be dried and deposited on or applied to a suitable adhesive backing to form a transdermal patch, covered with quick release paper or other layer for protection prior to use.

It will be understood that other transdermal delivery systems may also be used, such as lipoderm and anhydrous transdermal gels, for example. It has also been found that a somewhat higher dosage may be needed in some instances, e.g., 0.3 mcg rather than 0.2 mcg when using a karayaoum/glycerin delivery system rather than a PLO gel, and it is anticipated that variations in optimal dosage may occur in using other delivery systems as well.

c. DOSAGE RANGES

When administered by transdermally, the dosage range for methyl 4-imidazolecarboxylate is suitably from about 0.01 mcg per day to about 3.0 mcg per day; negligible effect has been observed using dosages below the lower figure, while dosages about the upper figure (i.e., above approximately 3.0 mcg per day) tend to produce a negative cognitive effects, in a form of mental haziness or sleepiness.

As will be described in the following examples, dosages in the range from about 0.1 mcg to about 0.2 mcg per day have been found generally preferable, with some variation on a patient by patient basis. Also, surprisingly, it will be seen from the following examples that a regimen of administering a suitable amount (typically 0.2 mcg) of the methyl 4-imidazolecarboxylate on a cyclic but non-daily basis was found to be particularly effective; in particular, a regimen of applying approximately 0.2 mcg once every three days (i.e., administering the compound one day, followed by a break of two days before the next administration) has been found especially effective for the majority of patients. While the mechanism behind this is not fully understood, it is believed that the effectiveness of the periodic regimen, with a resting period of about 48 hours between applications, may be due to an associated half life period (within the body of the patient) of the material or an agent that is produced by the material.

Although administration on a three-day cycle as described is therefore generally preferred, in has been found that administrating the material at other periodicities can also be effective, albeit generally to a somewhat lesser degree. For example, it has been found that in some instances beneficial effects can be sustained by administering approximately 0.1 mcg every other day, or by administering dosages below about 0.1 mcg on a daily basis.

d. EXAMPLES

The following illustrative examples relate to actual practice of the invention described above in the treatment of multiple sclerosis.

Example One

A 64-year-old female who had been suffering from multiple sclerosis (MS) for 51 years was treated in accordance with the method of the present invention. The patient suffered from debilitating intention tremors in her hands, poor balance, garbled speech, right foot tingling and right leg weakness, left foot tingling and weakness. Within 60 minutes of applying the first dose of 0.125 mcg methyl 4-imidazolecarboxylate via transdermal patch application, the intention tremors were alleviated, but noted some waxing and waning of other symptoms throughout the first day of treatment. All MS symptoms were alleviated by the second day of treatment. After the third consecutive day of treatment, the patient had no symptoms of MS and she was able to remain free of symptoms for the next 36 hours without applying the treatment of the present invention. After 36 hours of not administering the treatment, she reported that her MS symptoms were returning, she then applied 0.125 mcg methyl 4-imidazolecarboxylate via transdermal patch and her MS symptoms were alleviated within 30 minutes of applying the treatment. She administered 0.125 mcg methyl 4-imidazolecarboxylate per day for next 2 consecutive days and was again able to remain free of all of the MS symptoms while wearing the transdermal patch containing the treatment dose and then remained free of symptoms for the following 2 days not administering the treatment. The treatment of the present invention has successfully alleviated all of the MS symptoms plaguing this patient prior to the initiation of the methyl 4-imidazolecarboxylate, utilizing a dosing schedule of 0.2 mcg methyl 4-imidazolecarboxylate for one day followed by 2 consecutive days without administering treatment and then repeating such dosing schedule.

Example Two

A 46-year-old female who has been suffering from multiple sclerosis (MS) for 21 years was treated in accordance with the method of the present invention. The patient suffered from left foot tingling and numbness, left hand tingling and numbness, left leg weakness, slurred speech, cognitive impairment, fatigue, facial/jaw pain, and heaviness in limbs. Within 30 minutes of applying the first dose of 0.15 mcg methyl 4-imidazolecarboxylate via transdermal patch application, all MS symptoms were alleviated. The patient remained free of all MS symptoms with the administration of 0.15 mcg methyl 4-imidazolecarboxylate per day for the next two consecutive days. The patient was able to remain free of MS symptoms for 36 hours following the two consecutive days of application of present invention without use of treatment. After 36 hours of not using the present invention treatment, the patient experienced left foot tingling. The patient then applied 0.15 mcg methyl 4-imidazolecarboxylate per day via transdermal patch for two consecutive days and all MS symptoms alleviated. The patient was able to remain free of all MS symptoms for the next 4 days without applying the present invention treatment. On the fifth day without treatment, left foot tingling returned, so the patient applied 0.15 mcg methyl 4-imidazolecarboxylate via transdermal patch and symptoms resolved immediately. The following 5 days the patient remained free of all MS symptoms without administering treatment of present invention. The patient has continued to remain free of all MS symptoms utilizing a dosing schedule of 0.2 mcg methyl 4-imidazolecarboxylate applied via transdermal patch for one day and then without administering treatment for 2 consecutive days and then repeating such dosing schedule.

Example Three

Four MS patients, 2 female and 2 male, reported improvement in their MS symptoms i.e. improved bladder function, decreased fatigue, decreased tingling and numbness, improved balance, improved cognition and memory, improved walking ability, and improved sleep with vivid dreams, while being treated in accordance with the method of the present invention. Each patient has continued to maintain such improvements in their symptoms of MS by applying 0.2 mcg methyl 4-imidazolecarboxylate via transdermal patch for one day followed by two consecutive days without administering treatment and then repeating such dosing schedule.

Example Four

Six MS patients and one fibromyalgia patient reported improved cognitive function and improved memory while being treated in accordance with the method of the present invention. Prior to starting the treatment all 7 patients reported memory deficits, difficulty multi-tasking, and difficulty with word recall often resulting in dysphasia. After starting treatment all patients reported significant improvement in all of the preceding memory and cognitive deficits and these improvements have maintained while continuing on the treatment. One patient recalled a phone number that he had not used for 7 months. All patients reported a "clearing of the brain fog" meaning increased mental clarity, improved concentration, ability to multi-task again, improved short-term and long-term memory.

Example Five

A 48-year-old female who has been suffering from fibromyalgia for 10 years was treated in accordance with the method of the present invention. The patient reported decreased pain, decreased fatigue and improved mental clarity within hours of applying the first dose of 0.2 mcg methyl 4-imidazolecarboxylate. This patient has maintained has remained free of pain, and improved mental clarity while utilizing the dosing schedule of administering 0.2 mcg via transdermal patch for one day followed by two consecutive days of not administering the treatment and then repeating this one day on and two days off dosing schedule. The patient has reported only two incidences of increased fatigue, which lasted only one day per incidence, and these incidences were preceded by very stressful life events.

Example Six

Two male MS patients, a 39-year-old and a 42-year-old, experienced decreased libido, decreased penile sensation, and erectile dysfunction. Within three days of the first administration of the treatment of 0.2 mcg of methyl 4-imidazolecarboxylate, both patients reported increased libido, full erections, increased penile sensation, easily stimulated arousal, no premature ejaculation, greater volume of semen with ejaculation, stronger orgasms, ability to achieve a full erection in 1-3 minutes after first ejaculation. These improvements in sexual function have persisted while continuing on the treatment. The 39-year-old patient stopped the treatment for one week and during week of not using the treatment, the patient reported a decrease in libido and inability in achieving a full erection. His ability to achieve a full erection numerous times following repeated ejaculations was restored the same day that he resumed the treatment.

Example Seven

A 64 year old female with a family history of depression and has a personal history of major clinical depression. Hospitalized in 1975 and again in 1990 with major episodes of depression including extreme suicidal ideations. Numerous medications were tried to help stabilize her condition. Since 1990 she has been taking 25 mg to 75 mg of nortriptyline to manage her depression and reports having to increase the dose to has high as 100 mg during stressful life events. The patient reported dry mouth and constipation as side effects of using nortriptyline.

The patient reported suffering from the following symptoms despite taking nortriptyline:
Decreased energy, fatigue
Early morning awakening The patient reported increased energy the first day of initiating the treatment of 0.2 mcg methyl 4-imidizolecarboxylate and reported sleeping until the alarm clock went off in the morning. She also reported very vivid dreams and she was able to recall the details of her dreams easily. She has remained free of all symptoms of depression while continuing on the treatment, applying 0.2 mcg methyl 4-imidazolecarboxylate via transdermal patch for one day followed by no treatment for two consecutive days and then repeating this dosing schedule of one day on and two days off with no side effects. Her constipation and dry mouth have resolved as well. She also has reported that her hair is regaining its original pigment and that her eyebrows are coming in darker and thicker resembling her younger years.

It is to be recognized that various alterations, modifications, and/or additions may be introduced into the construction and arrangements of parts described above without departing from the spirit or ambit of the present invention as defined by the appended claims.

What is claimed is:

1. A method for treatment of multiple sclerosis, comprising:
    administering to a patient suffering from said multiple sclerosis, a therapeutically effective amount methyl 4-imidazolecarboxylate.

2. The method of claim 1, wherein the step of administering to said patient a therapeutically effective amount of methyl 4-imidazolecarboxylate comprises:
    administering a therapeutically effective amount of methyl 4-imidazolecarboxylate to said patient by transdermal application.

3. The method of claim 2, wherein the step of administering a therapeutically effective amount of methyl 4-imidazolecarboxylate to said patient by transdermal application comprises:
    administering methyl 4-imidazolecarboxylate to said patient in a dosage in the range from about 0.01 mcg per day to about 3.0 mcg per day.

4. The method of claim 3, wherein the step of administering methyl 4-imidazolecarboxylate to said patient in a dosage in the range from about 0.01 mcg per day to about 3.0 mcg per day comprises:
    administering methyl 4-imidazolecarboxylate to said patient in a dosage in the range from about 0.1 mcg per day to about 0.2 mcg per day.

5. The method of claim 1, wherein the step of administering to said patient a therapeutically effective amount of methyl 4-imidazolecarboxylate comprises:
    administering said methyl 4-imidazolecarboxylate on a non-daily cycle, allowing a period of at least one day between each day on which said effective amount of methyl 4-imidazolecarboxylate is administered.

6. The method of claim 5, wherein the step of administering said methyl 4-imidazolecarboxylate on a non-daily cycle comprises:
    administering said methyl 4-imidazolecarboxylate on an approximate three-day cycle, allowing about two days between each day on which said therapeutically effective amount of methyl 4-imidazolecarboxylate is administered.

7. The method of claim 6, wherein the step of administering a therapeutically effective amount of methyl 4-imidazolecarboxylate comprises:
    administering said therapeutically effective amount of methyl 4-imidazolecarboxylate by transdermal application.

8. The method of claim 7, wherein the step of administering said therapeutically effective amount of methyl 4-imidazolecarboxylate comprises:
    administering said methyl 4-imidazolecarboxylate in an amount of about 0.2 mcg.

* * * * *